US012561402B2

(12) United States Patent
Tirupathi et al.

(10) Patent No.: US 12,561,402 B2
(45) Date of Patent: Feb. 24, 2026

(54) IDENTIFICATION OF A SECTION OF BODILY TISSUE FOR PATHOLOGY TESTS

(71) Applicant: International Business Machines Corporation, Armonk, NY (US)

(72) Inventors: Seshu Tirupathi, Dublin (IE); Jonathan Peter Epperlein, Dublin (IE); Pol Mac Aonghusa, Carbury (IE); Rahul Nair, Dublin (IE); Sergiy Zhuk, Dublin (IE); Mykhaylo Zayats, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1006 days.

(21) Appl. No.: 17/097,220

(22) Filed: Nov. 13, 2020

(65) Prior Publication Data

US 2022/0156606 A1 May 19, 2022

(51) Int. Cl.
*G06N 20/00* (2019.01)
*G06F 18/214* (2023.01)
(Continued)

(52) U.S. Cl.
CPC ............. *G06F 18/24* (2023.01); *G06N 20/00* (2019.01); *G06T 7/0016* (2013.01); *G16H 15/00* (2018.01);
(Continued)

(58) Field of Classification Search
None
See application file for complete search history.

(56) References Cited

U.S. PATENT DOCUMENTS 6,175,759 B1   1/2001   Chan et al.
6,785,409 B1   8/2004   Suri
(Continued)

FOREIGN PATENT DOCUMENTS

CN     107909102 A     4/2018
CN     110893095 A     3/2020
(Continued)

OTHER PUBLICATIONS

Lancaster, Gemma, Aneta Stefanovska, Margherita Pesce, Gian Marco Vezzoni, Barbara Loggini, Raffaele Pingitore, Fabrizio Ghiara et al. "Dynamic markers based on blood perfusion fluctuations for selecting skin melanocytic lesions for biopsy." Scientific Reports 5, No. 1 (2015): 12825.) (Year: 2015).*
(Continued)

*Primary Examiner* — Vincent Gonzales
(74) *Attorney, Agent, or Firm* — Amin, Turocy & Watson, LLP

(57) ABSTRACT

Embodiments are provided for identification of a section of bodily tissue as either a candidate or a non-candidate for pathology tests. In some embodiments, a system can include a processor that executes computer-executable components stored in memory. The computer-executable components can include a feature composition component that generates a feature vector representing a physical model describing dye dynamics that determines a group of multispectral images of a section of bodily tissue. The computer-executable components also can include a classification component that generates a classification attribute for the section of bodily tissue by applying a classification model to the feature vector. The classification attribute designates the section of bodily tissue as one of biopsy-candidate or non-biopsy-candidate.

25 Claims, 12 Drawing Sheets
(Continued)

(3 of 12 Drawing Sheet(s) Filed in Color)

(51) Int. Cl.

| | |
|---|---|
| *G06F 18/24* | (2023.01) |
| *G06T 7/00* | (2017.01) |
| *G16H 15/00* | (2018.01) |
| *G16H 30/40* | (2018.01) |
| *G16H 50/20* | (2018.01) |
| *G16H 50/50* | (2018.01) |

(52) U.S. Cl.
CPC ............. *G16H 30/40* (2018.01); *G16H 50/20* (2018.01); *G16H 50/50* (2018.01); *G06T 2207/10036* (2013.01); *G06T 2207/10064* (2013.01); *G06T 2207/20076* (2013.01)

(56) References Cited

U.S. PATENT DOCUMENTS

| | | | |
|---|---|---|---|
| 9,060,685 | B2 | 6/2015 | Cosatto et al. |
| 9,848,843 | B2 | 12/2017 | Grass et al. |
| 9,892,513 | B2 | 2/2018 | Gurevich et al. |
| 10,255,693 | B2 | 4/2019 | Smith |
| 10,783,636 | B2 | 9/2020 | Gurevich et al. |
| 11,145,052 | B2 | 10/2021 | Epperlein et al. |
| 2006/0115146 | A1 | 6/2006 | Ogura et al. |
| 2009/0190812 | A1 | 7/2009 | Sano et al. |
| 2014/0227726 | A1* | 8/2014 | Ataullakhanov ........ C12Q 1/56 435/23 |
| 2015/0023573 | A1 | 1/2015 | Sato et al. |
| 2016/0035093 | A1 | 2/2016 | Kateb et al. |
| 2016/0253800 | A1 | 9/2016 | Gurevich et al. |
| 2016/0314580 | A1 | 10/2016 | Lloyd et al. |
| 2017/0084024 | A1 | 3/2017 | Gurevich |
| 2017/0367580 | A1* | 12/2017 | DiMaio .................. A61B 5/445 |
| 2018/0028079 | A1 | 2/2018 | Gurevich et al. |
| 2018/0341747 | A1* | 11/2018 | Bernard ................. A61B 5/002 |
| 2020/0193597 | A1 | 6/2020 | Fan et al. |

FOREIGN PATENT DOCUMENTS

| | | |
|---|---|---|
| EP | 3593357 | 1/2020 |
| WO | 2015054666 | 4/2015 |
| WO | 2018075679 | 4/2018 |
| WO | 2018165103 | 9/2018 |
| WO | 2022/101823 A1 | 5/2022 |

OTHER PUBLICATIONS

Socolofsky, Scott A.; Jirka, Gerhard H. "Advective Diffusion Equation" (PDF). Lecture notes. Archived from the original (PDF) on Jun. 25, 2010. Retrieved Dec. 6, 2023. 18 pages. (Year: 2010).*
Janowczyk, Andrew, and Anant Madabhushi. "Deep learning for digital pathology image analysis: A comprehensive tutorial with selected use cases." Journal of pathology informatics 7, No. 1 (2016): 29. (Year: 2016).*
Levenson, Richard M., and James R. Mansfield. "Multispectral imaging in biology and medicine: slices of life." Cytometry Part A: the journal of the International Society for Analytical Cytology 69, No. 8 (2006): 748-758. (Year: 2006).*
Gao, Zhifan, Xin Wang, Shanhui Sun, Dan Wu, Junjie Bai, Youbing Yin, Xin Liu, Heye Zhang, and Victor Hugo C. de Albuquerque. "Learning physical properties in complex visual scenes: An intelligent machine for perceiving blood flow dynamics from static CT angiography imaging." Neural Net. 2020: 82-93. (Year: 2020).*
Mell et al., "The NIST Definition of Cloud Computing," Recommendations of the National Institute of Standards and Technology, NIST Special Publication 800-145, Sep. 2011, 7 pages.
Halicek et al., "In-Vivo and Ex-Vivo Tissue Analysis through Hyperspectral Imaging Techniques: Revealing the Invisible Features of Cancer," Cancers, 11, 756, 2019; 30 pages.
Khokhar, et al., "Illuminating neoplasia with systemic indocyanine green and near-infrared endoscopic system—clinical experience (AB027. 172)." Mesentery and Peritoneum, vol. 2, No. 2, 2018, 1 page.
Akbari et al., "Cancer detection using infrared hyperspectral imaging." Cancer Sci, Apr. 2011, vol. 102, No. 4, pp. 852-857, 2011.
Valdes et al. "Optical technologies for intraoperative neurosurgical guidance." Neurosurgical Focus, vol. 40, 3, 2016: E8. doi:10.3171/2015.12.FOCUS15550; 35 pages.
Zhuk et al., "Perfusion Quantification from Endoscopic Videos: Learning to Read Tumor Signatures," [Submitted on Jun. 25, 2020], https://arxiv.org/abs/2006.14321; 11 pages.
Bizzego et al., "Evaluating reproducibility of AI algorithms in digital pathology with DAPPER," PLoS Comput Biol 15(3): e1006269; Mar. 27, 2019; 15 pages.
Thatcher et al., "Imaging Techniques for Clinical Burn Assessment with a Focus on Multispectral Imaging," Advances in Wound Care, vol. 5, No. 8, pp. 360-378, 2016.
Gurfinkel et al., "Pharmacokinetics of ICG and HPPH-car for the Detection of Normal and Tumor Tissue Using Fluorescence, Near-infrared Reflectance Imaging: A Case Study." Photochemistry and Photobiology, vol. 72, No. 1, Jul. 2000, pp. 94-102.
Epperlein et al., "Biophysics-Inspired AI Uses Photons to Help Surgeons Identify Cancer." Feb. 28, 2019. [Accessed Apr. 18, 2019] https://www.ibm.com/blogs/research/2019/02/biophysics-inspired-ai/; 3 Pages.
List of IBM Patents or Patent Applications Treated as Related.
IBM Research Blog: Biophysics-Inspired AI Uses Photons to Help Surgeons Identify Cancer.
International Search Report and Written Opinion received for PCT Application Serial No. PCT/IB2021/060454 dated Mar. 2, 2022, 10 pages.
Eren et al. "Assessment of Microcirculation of an Axial Skin Flap Using Indocyanine Green Fluorescence Angiography", Plastic and Reconstructive Surgery, Dec. 1995, pp. 1636-1649, vol. 96, Issue No. 7.

\* cited by examiner

S(x,y)
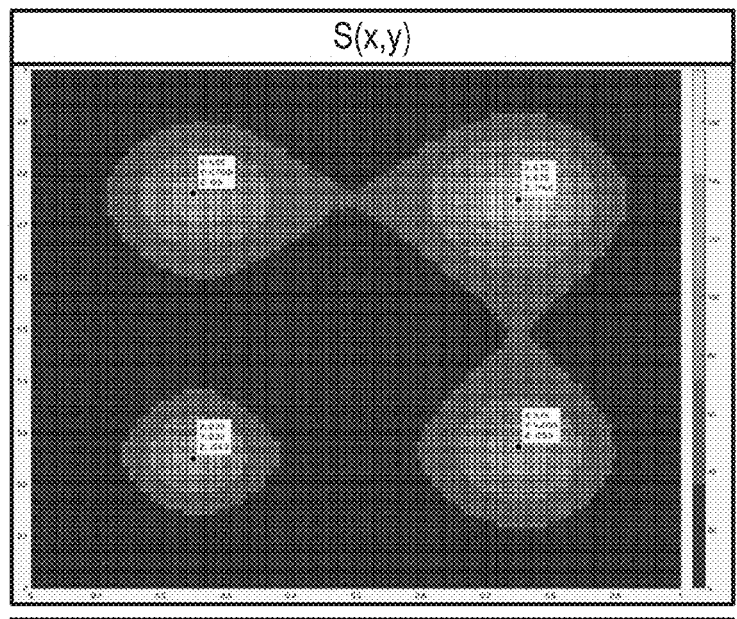
A(x,y)
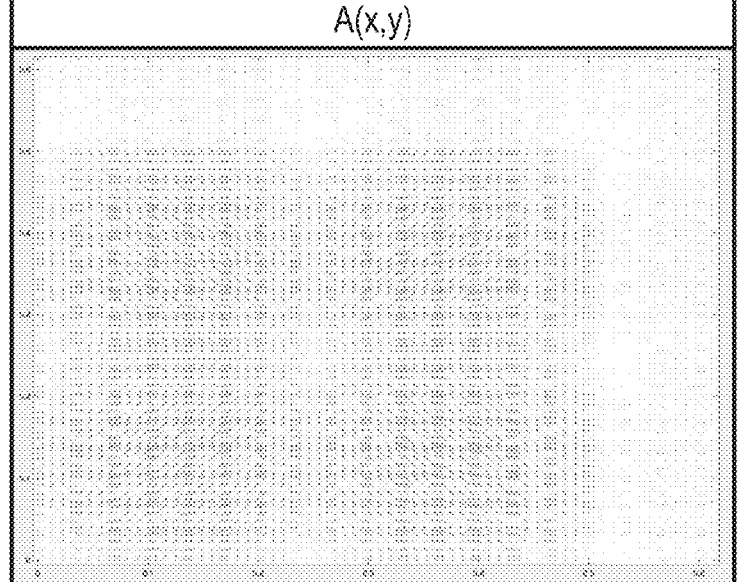
D(x,y)
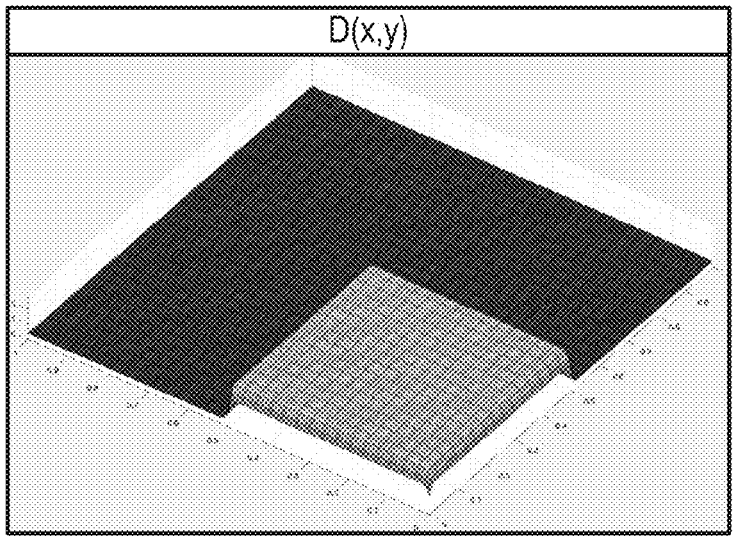
FIG. 5

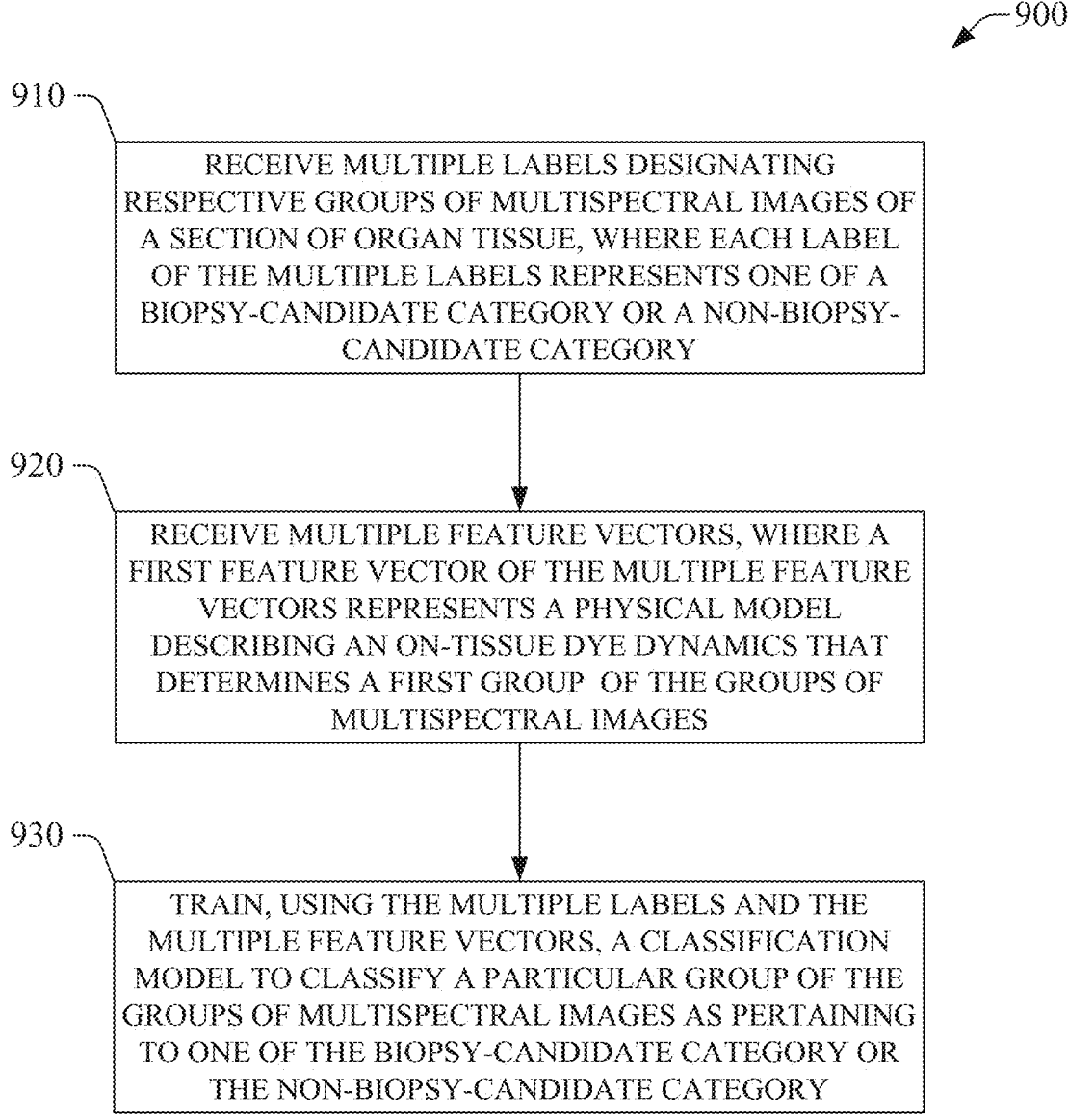

900

910 —

RECEIVE MULTIPLE LABELS DESIGNATING
RESPECTIVE GROUPS OF MULTISPECTRAL IMAGES OF
A SECTION OF ORGAN TISSUE, WHERE EACH LABEL
OF THE MULTIPLE LABELS REPRESENTS ONE OF A
BIOPSY-CANDIDATE CATEGORY OR A NON-BIOPSY-
CANDIDATE CATEGORY

920 —

RECEIVE MULTIPLE FEATURE VECTORS, WHERE A
FIRST FEATURE VECTOR OF THE MULTIPLE FEATURE
VECTORS REPRESENTS A PHYSICAL MODEL
DESCRIBING AN ON-TISSUE DYE DYNAMICS THAT
DETERMINES A FIRST GROUP OF THE GROUPS OF
MULTISPECTRAL IMAGES

930 —

TRAIN, USING THE MULTIPLE LABELS AND THE
MULTIPLE FEATURE VECTORS, A CLASSIFICATION
MODEL TO CLASSIFY A PARTICULAR GROUP OF THE
GROUPS OF MULTISPECTRAL IMAGES AS PERTAINING
TO ONE OF THE BIOPSY-CANDIDATE CATEGORY OR
THE NON-BIOPSY-CANDIDATE CATEGORY

FIG. 9

IDENTIFICATION OF A SECTION OF BODILY TISSUE FOR PATHOLOGY TESTS

BACKGROUND

The subject disclosure relates to identification of a section of bodily tissue as either a candidate or a non-candidate for pathology tests.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later.

According to an embodiment, a system is provided. The system includes a processor that executes computer-executable components stored in memory. The computer-executable components include a feature composition component that generates a feature vector representing a physical model describing dye dynamics that determines a group of multispectral images of a section of bodily tissue. The computer-executable components also include a classification component that generates a classification attribute for the section of bodily tissue by applying a classification model to the feature vector. The classification attribute designates the section of bodily tissue as one of biopsy-candidate or non-biopsy-candidate.

According to another embodiment, a computer-implemented method is provided. The computer-implemented method includes generating, by a computing system operatively coupled to a processor, a feature vector representing a physical model describing dye dynamics that determines a group of multispectral images of a section of bodily tissue. The computer-implemented method also includes generating, by the computing system, a classification attribute for the section of bodily tissue by applying a classification model to the feature vector. The classification attribute designates the area of human tissue as one of biopsy-candidate or non-biopsy-candidate.

According to yet another embodiment, a system is provided. The system can include a processor that executes computer-executable components stored in memory. The computer-executable components include an ingestion component that receives multiple feature vectors. A first feature vector of the multiple feature vectors represents a physical model describing on-tissue dye dynamics that determines a first group of groups of multispectral images of a section of bodily tissue. The computer-executable components also include a constructor component that trains, using the multiple feature vectors, a classification model to classify a particular group of the groups of multispectral images as pertaining to one of a biopsy-candidate category or a non-biopsy-candidate category.

According to still another embodiment, a computer-implemented method is provided. The computer-implemented method includes receiving, by a computing system operatively coupled to a processor, multiple feature vectors. A first feature vector of the multiple feature vectors represents a physical model describing on-tissue dye dynamics that determines a first group of groups of multispectral images of a section of bodily tissue. The computer-implemented method also includes training, by the computing system, using the multiple feature vectors, a classification model to classify a particular group of multispectral images as pertaining to one of a biopsy-candidate category or a non-biopsy-candidate category.

According to a further embodiment, a computer program product for identification of a section of bodily tissue as either a candidate or a non-candidate for a pathology test. The computer program product includes a computer-readable storage medium having program instructions embodied therewith. The program instructions are executable by a processor to cause the processor to generate a feature vector representing a physical model describing on-tissue dye dynamics that determines a group of multispectral images of a section of bodily tissue. The program instructions also are executable by the processor to cause the processor to generate a classification attribute for the section of bodily tissue by applying a classification model to the feature vector. The classification attribute designates the area of human tissue as one of biopsy-candidate or non-biopsy-candidate.

Although embodiments of this disclosure are described in connection with an organ and organ tissue, the disclosure is not limited in that respect. The principles of this disclosure can be applied to other types of bodily tissue that can be probed using photoluminescence of a dye substance that can propagate through the bodily tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 illustrates non-limiting examples of spatially-resolved parameters of a physical model that can determine time-resolved fluorescence of a dye substance transported through an organ, in accordance with one or more embodiments described herein.

FIG. 9 is a flowchart of a non-limiting example of a computer-implemented method for generating a classification model for classification of a section of organ tissue as either a candidate on a non-candidate for a pathology test, in accordance with one or more embodiments described herein.

DETAILED DESCRIPTION

Figure 1:
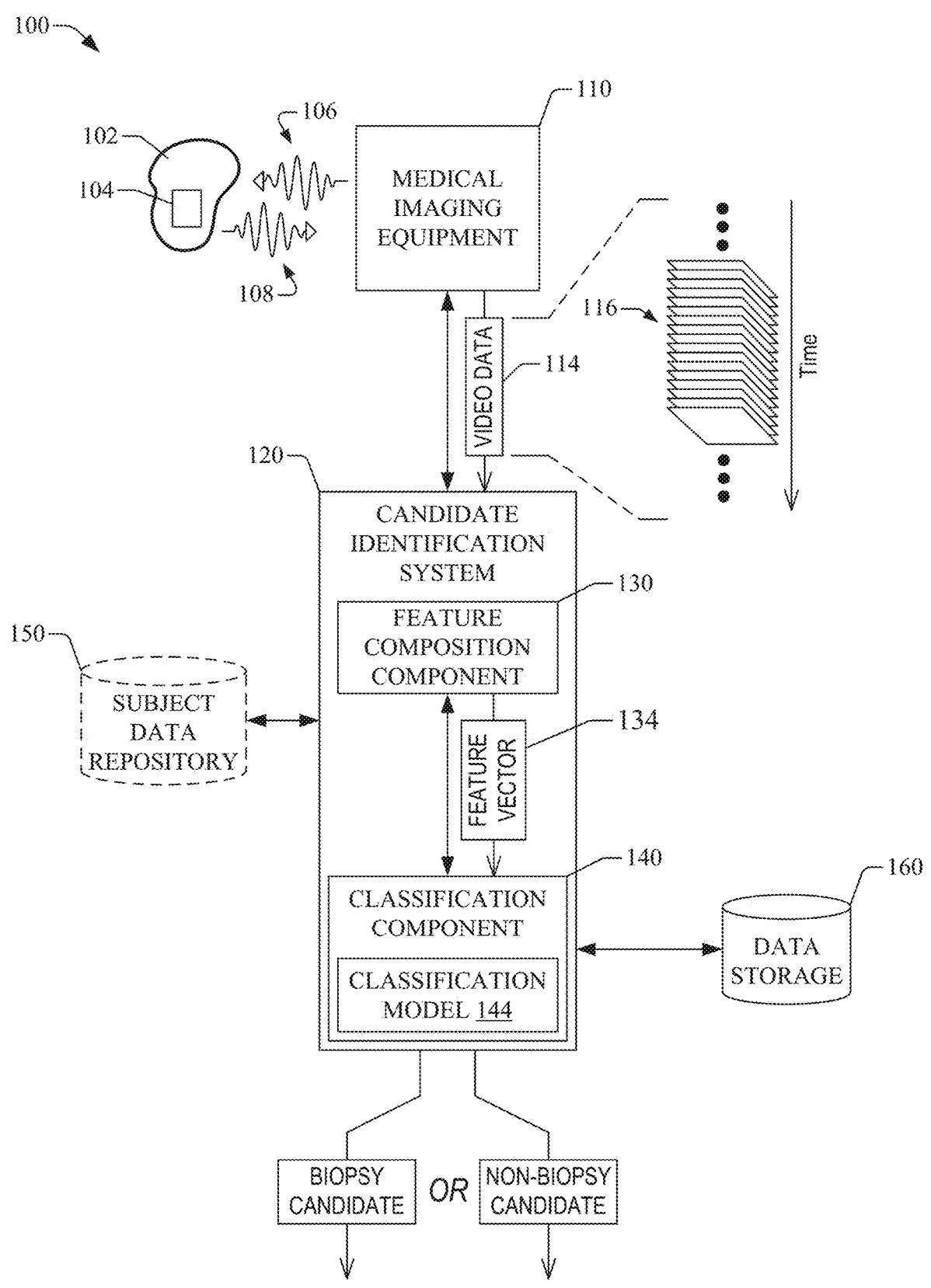
FIG. 1 illustrates a non-limiting example of an operational environment for identification of a section of organ tissue as either a candidate or a non-candidate for pathology tests, in accordance with one or more embodiments described herein.

Embodiments of this disclosure address the issue of identification of a section of organ tissue as either a candidate or a non-candidate for pathology tests. Deciding on which section of organ tissue to select for specimen collection for a pathology test can be time consuming. It also can be expensive because such a decision typically involves a surgeon. The surgeon can examine an organ and can decide which specimens are sent for pathology tests in order to check for existence, causes, and/or effects of diseases or disease complications. The surgeon commonly relies on the observation of the flow of a dye substance that is fluorescent and has been administered to a subject having the organ. The blood stream of the subject transports the dye substance through the organ. Such a transport mechanism is referred to as perfusion. Fluorescence, and more generally, photoluminescence, is a non-invasive mechanism that can reveal the presence or absence of the dye substance in sections of the organ. Fluorescence also can be used to visualize blood flow patterns within the organ. Peculiarities of the transport of the dye substance on the organ can provide information related to the health of a section of organ tissue—e.g., cancerous tissue can retain the dye substance much longer than healthy tissue does. Those peculiarities, however, are typically represented by changes in fluorescence intensity. As such, the identification of changes arising from unhealthy organ tissue is highly subjective and qualitative at best. As a result, the number of samples of organ tissue that is collected for pathology tests can be excessive.

Embodiments of the disclosure provide a classification model that can designate a section of organ tissue or another type of bodily tissue as a candidate for a biopsy or a non-candidate for the biopsy. The classification model can be trained on large amounts of labeled data using machine-learning techniques. The labeled data can include feature vectors determined using multispectral video segments of sections of organ tissue that have been analyzed and labeled as having pathologic changes or lacking pathologic changes. Those video segments can be generated using photoluminescence, such as fluorescence, of dye substances, in some embodiments. A feature vector for a particular one of the video segments can be generated by determining a set of parameters defining a physical model that describes the transport of the dye substance through the organ tissue. Accordingly, multiple feature vectors and respective labels can be used to train the classification model. Because of the large amount of video segments and respective labels, the classification model that is trained can remove the subjectivity in the analysis of photoluminescence (fluorescence, for example) of a dye substance when probing a new section of organ tissue.

Embodiments of the disclosure can generate a feature vector using a sequence of frames of a multispectral video segment of an organ being probed using fluorescence or, more generally, photoluminescence of a dye substance. The feature vector includes parameters that define a physical model that described the transport of the dye substance through the organ. A trained classification model can be applied to the feature vector in order to identify a section of the organ as either a candidate or a non-candidate for a pathology test.

By providing a machine-learning dictated way of deciding section of organ tissue or another type of bodily tissue to be sent to pathology, embodiments of this disclosure provide several advantages over commonplace approaches and technologies. One of such advantages can include the automation of surgical intervention. Another one of such advantages can include faster and cheaper alternative for medical examination, with potentially reduced collection of tissue samples for pathology tests. Such a reduction can be accomplished by efficiently, yet judiciously, identifying sections of organ tissue that may require pathology analysis.

With reference to the drawings, FIG. 1 illustrates a non-limiting example of an operational environment 100 for identification of a section of organ tissue as either a candidate or a non-candidate for pathology tests, in accordance with one or more embodiments described herein. In the operational environment 100, an organ 102 can be probed using fluorescence of a dye substance that has been injected into a subject, such as a human or another type of mammal. To that end, medical imaging equipment 110 can emit excitation light 106 onto the organ 102 and, in response, can collect emitted light 108 from the organ 102. The emitted light 108 is emitted through fluorescence of the dye substance. In one example, the dye substance can include indocyanine green (ICG). The excitation light 106 can be either essentially monochromatic light or polychromatic light. The emitted light 108 can be polychromatic having wavelengths that span a wide region of the electromagnetic radiation spectrum. Those wavelengths can be dictated by the type of the dye substance.

The medical imaging equipment 110 can include one or several camera devices (not depicted in FIG. 1). Each one of the camera device(s) can detect light in a particular portion of the electromagnetic (EM) radiation spectrum. In embodiments in which the medical imaging equipment 110 includes several camera devices, two or more of the particular portions of the EM radiation spectrum can be at least partially overlapping. To detect light, a camera device can include an imaging sensor device having one or more photodetectors (an array of photodiodes, for example), active amplifiers, and the like. In some embodiments, the imaging sensor device can include a semiconductor-based sensor having multiple semiconducting photosensitive elements. For instance, the imaging sensor devices can be embodied in or can include a charge-coupled device (CCD) camera; an active-pixel sensor or other type of complementary metal-oxide semiconductor (CMOS) based photodetector; an array of multi-channel photodiodes; a combination thereof; or the like.

In some embodiments, the medical imaging equipment 110 can include several camera devices. A first camera device of those camera devices can detect light in the visible portion of the EM radiation spectrum—e.g., the first camera device can sense photons having energies in a range from about 1.63 electronvolt (eV) to about 3.26 eV. In addition, a second camera device of the several camera devices can detect light in the IR portion of the EM radiation spectrum—e.g., the second camera device can sense photons having energies in a range from about 1.24 meV to about 1.63 eV.

The medical imaging equipment 110 can generate video signal using the camera device(s). The video signal can include visible video signal or IR video signal, or a combination of both. The visible video signal can include first video data defining a sequence of frames, where each frame can represent a digital image of a section 104 of the organ 102 that is formed using visible light. The IR video signal can include second video data defining another sequence of frames, where each frame can represent a digital image of the section 104 of the organ 102 that is formed using IR light. Visible frames and infrared frames can be generated at respective acquisition rates, in some cases. Accordingly, video signal generated by the medical imaging equipment 110 can constitute multispectral videos, where each multispectral video includes a group of multispectral images. It is noted that the section 104 can contain one or several particular subsections (not depicted in FIG. 1) representing respective regions of interest (ROIs). A ROI is itself a section of the organ 102.

As is illustrated in FIG. 1, the medical imaging equipment 110 can send video data 114 defining a sequence of frames 116 to a candidate identification system 120. In some cases, the medical imaging equipment 110 can send the video data 114 to the candidate identification system 120 in essentially real-time, as video signal is generated by the medical imaging equipment 110. The video data 114 can include visible video data or IR video data, or a combination of both. In some embodiments, the video data 114 is prestored in the candidate identification system 120 and can originate from the medical imaging equipment 110 or from another source or repository.

Figure 2A:
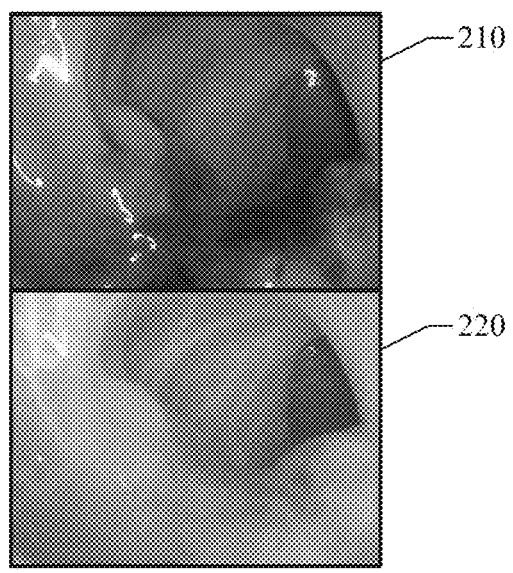
FIG. 2A illustrates non-limiting examples of an image of an organ acquired using visible light and an image of the organ acquired using infrared (IR) light, in accordance with one or more embodiments described herein.
Figure 2B:
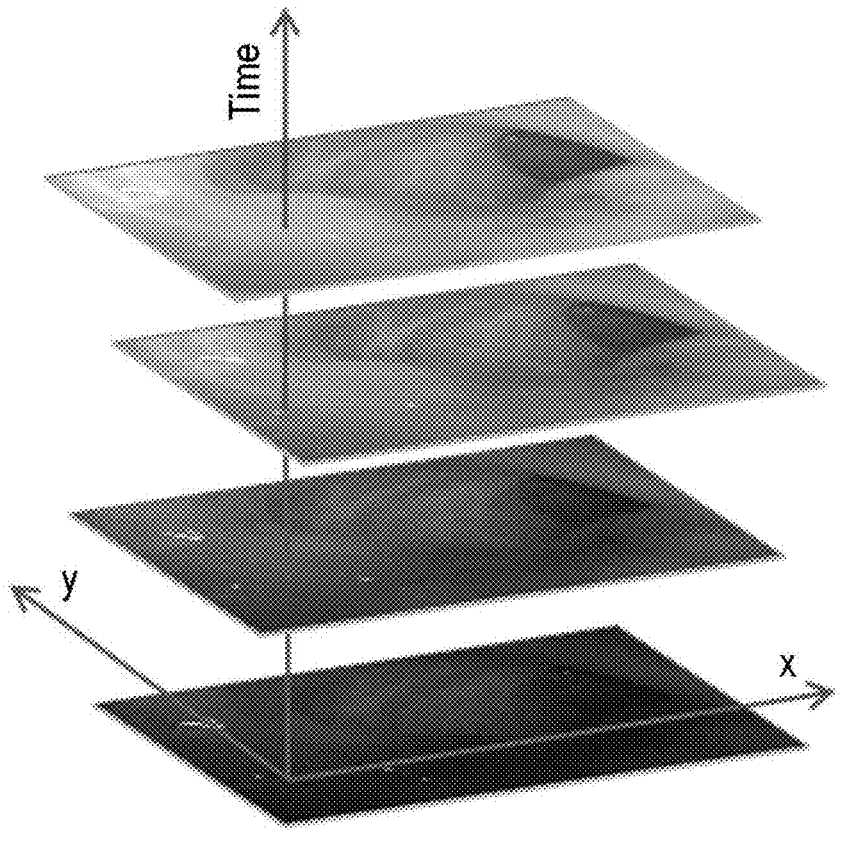
FIG. 2B illustrates a non-limiting example of a sequence of frames corresponding to images of an organ acquired using IR light, in accordance with one or more embodiments described herein.

The sequence of frames 116 can include a group of multispectral images of the section 104 of the organ 102. More specifically, a frame in the sequence of frames 116 represents a multispectral image of that group of multispectral images. The medical imaging equipment 110 can track the movement of the organ 102 in order to generate each frame of the sequence of frames 116 relative to a coordinate system (such as a Cartesian coordinate system) fixed on the organ 102. Accordingly, each frame of the sequence of frames 116 can represent a cross-sectional multispectral image of the organ 102 on a two-dimensional plane relative to that coordinate system. For purposes of illustration, FIG. 2A presents an example of a frame 210 corresponding to an image of the section 104 acquired using visible light. FIG. 2A also presents an example of a frame 220 corresponding to a section 104 acquired using IR light. As a further illustration, FIG. 2B presents images acquired using IR light. Those images can correspond to frames including in the sequence of frames 116. Those images represent a cross-section of the organ 102 on a two-dimensional plane relative to a coordinate system affixed on the organ 102.

Figure 3:
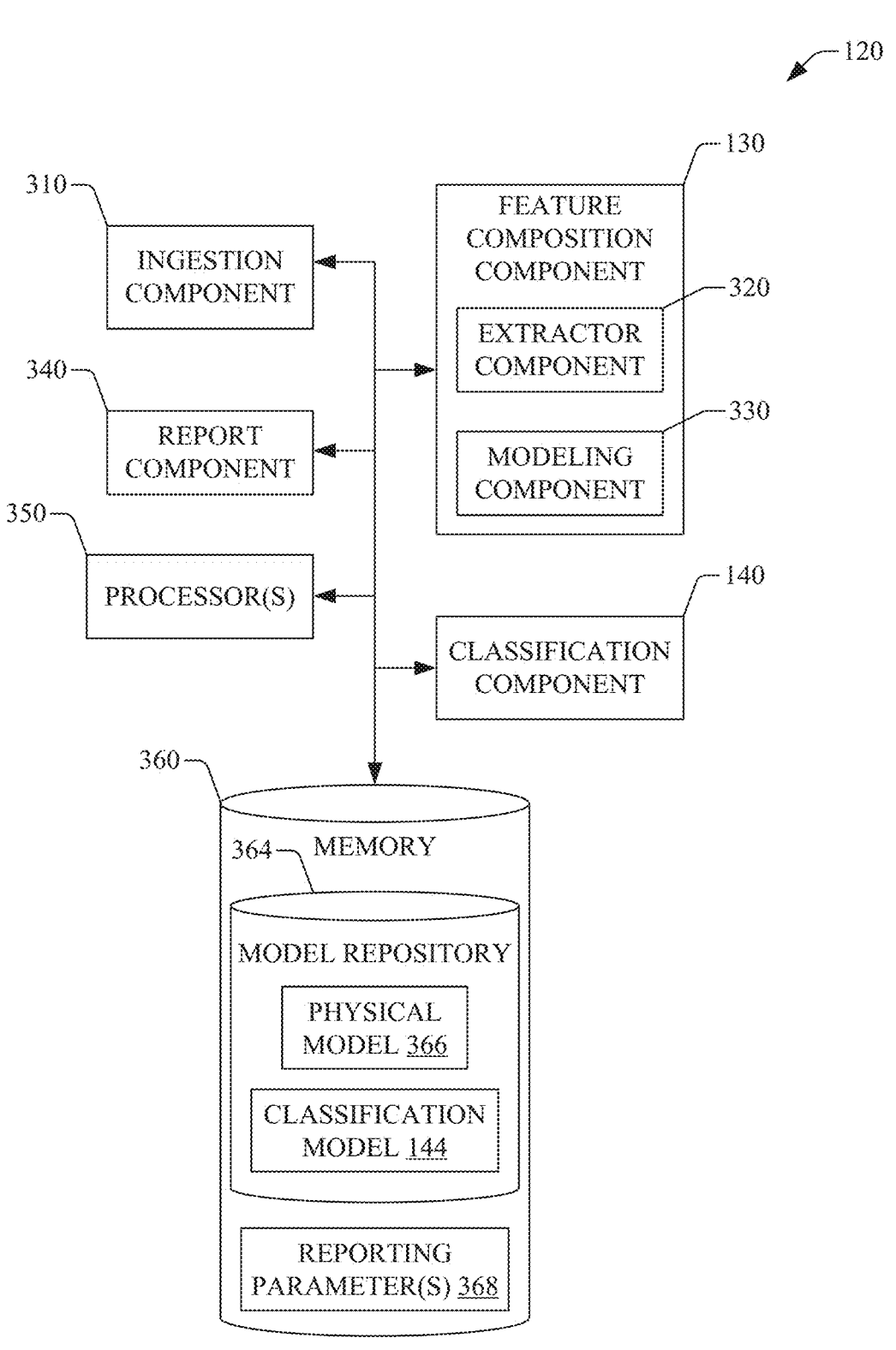
FIG. 3 is a block diagram of a non-limiting example of a system for identification of a section of organ tissue as either a candidate or a non-candidate for pathology tests, in accordance with one or more embodiments described herein.

The candidate identification system 120 can receive the video data 114 and can identify, using the video data 114, the section 104 of organ tissue as being either a candidate for biopsy or a non-candidate for biopsy. To perform such identification, the candidate identification system 120 can include a feature composition component 130 that can generate a feature vector 134 corresponding to the video data 114. In some embodiments, the candidate identification system 120 can include an ingestion component 310 (FIG. 3) that can receive the video data 114 from the medical imaging equipment 110. The ingestion component 310 can supply the video data 114 to the feature composition component 130. As is illustrated in FIG. 3, the candidate identification system 120 also can include one or many processors 350, multiple components, and data repositories, including one or many memory devices 360 (referred to as memory 360). The one or many processors, the multiple components, and the data repositories can be electrically, optically and/or communicatively coupled to one another.

With further reference to FIG. 1, the feature vector 134 includes parameters defining a physical model describing on-tissue dynamics of the dye substance transported through the organ 102. In some embodiments, a parametrization of the physical model can be retained in a model repository 364 (FIG. 3) within the memory 360. Such a physical model can thus determine, at least partially, a time series of imaging data corresponding to the group of multispectral images of the sequence of frames 116. In some configurations, the imaging data can be indicative of an average image brightness across the section 104. That is, in one example, the imaging data can be indicative of an average of observed brightness values of respective pixels spanning an image of the section 104. Accordingly, the time series of imaging data can represent a time-resolved fluorescence profile without spatial dependence across the section 104. In other configurations, the imaging data can be spatially-resolved. That is, the imaging data can be indicative of an image brightness at a position (x, y) corresponding to one or several pixels in a multispectral image. Accordingly, a time series of imaging data can be determined for each position (x, y). As such, in some configurations, a time-resolved fluorescence profile corresponding to the section 104 can be said to be "spatially distributed."

In some embodiments, the physical model can include a perfusion model that describes the on-tissue dye dynamics via an advection-diffusion equation in two-dimensional space, as is shown in Eq. (1):

$$C_t + \nabla \cdot (A\, C_t) - \nabla \cdot (D \nabla C_t) = S\; e^{-\frac{t-t_0}{\tau}} \qquad (1)$$

Here, $C_t = C(t, x, y)$ represents concentration of dye substance at a time t and position (x, y). Without intending to be bound by theory and/or modeling, because the dye substance is fluorescent, such a concentration can be represented by an intensity of the emitted light 108 at the position (x, y) at the time t. In addition, $A = A(x, y)$ represents an advection vector-field coefficient; D(x, y) represents an isotropic diffusion coefficient; and S(x, y) represents intensity of a source of the advection-diffusion equation. The source distribution S(x, y) can determine, at least partially, the spatially-resolved time series of fluorescence intensities. Further, ti is a relaxation time and to represents the time at which the diffusion of the dye substance started. In some embodiments, the physical model also can include a photon diffusion equation describing photon fluence rate distribution across the section 104 or a ROI contained in the section 104.

By imaging the section 104 of the organ 102 using fluorescence of the dye substance, $C_t$ in Eq. (1) can be known from the observed emitted light 108. Therefore, A(x, y), and D(x, y), and S(x, y) at a time t can be determined from the physical model and time series of imaging data. Such a determination is referred to as a "model inversion" solution. The feature vector 134 can thus include position-dependent parameters (A(x, y), D(x, y), S(x, y)), where (x, y) represents a point in the grid of points relative to the coordinate system at a section of organ tissue (such as the section 104 or a ROI therein). As a result, each point in that grid can have a corresponding feature vector 134. Such a feature vector 134 can be referred to as a spatially-resolved feature vector. In embodiments in which the physical model also includes a photon diffusion equation, the spatially-resolved feature vector can include other position-dependent parameters, such as optical absorption coefficients and/or light scattering coefficients. The optical absorption coefficient and the light scattering coefficients can be determined from the photon diffusion equation.

Figure 4:
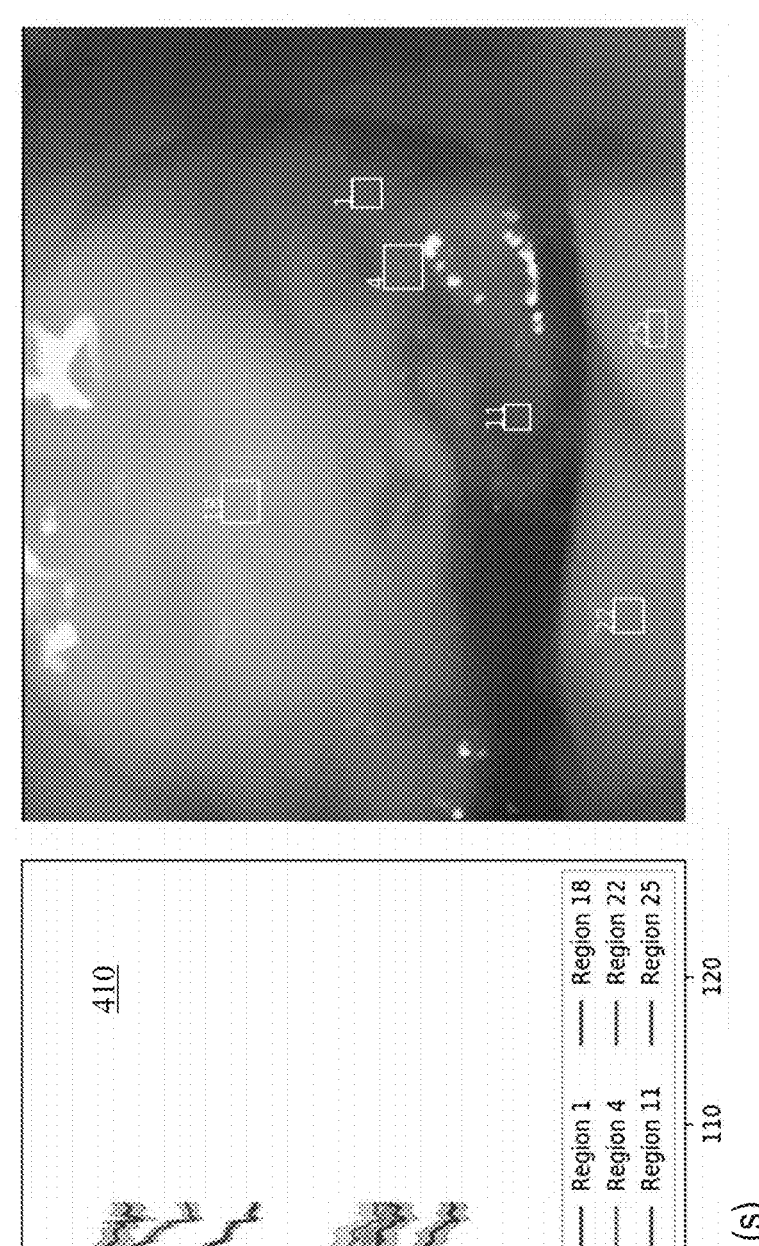
FIG. 4 illustrates non-limiting examples of time-resolved fluorescence profiles for several sections of organ tissue, in accordance with one or more embodiments described herein.

In some embodiments, to determine a solution to the model inversion problem, and thus generate the feature vector 134, the feature composition component 130 can include an extractor component 320 (FIG. 3). The extractor component 320 can generate a time series of imaging data using the group of multispectral images corresponding to the sequence of frames 116. To that end, the extractor component 320 can select a spatial resolution (a number of pixels, for example) and can then determine brightness intensities I{(t; x, y)} at a time t, for respective points {(x, y)} in a two-dimensional grid of points having a pitch defined by the spatial resolution. The extractor component 320 can determine {I(t; x, y)} by averaging observed brightness values corresponding to respective pixels for the spatial resolution, for example. In some cases, the selected spatial resolution can span the entirety of pixels present in a ROI within the section 104. Again, the ROI also is a section of organ tissue of the organ 102. To illustrate such cases, FIG. 4 presents examples of time-resolved fluorescence profiles <I(t)> for respective sections of organ tissue. Here, <•> indicates spatial average. Those sections are labeled "Region 1," "Region 4," "Region 11," "Region 18," "Region 22," and "Region 25," simply for the sake of nomenclature.

Further, also to generate the feature vector, the feature composition component 130 can include a modeling component 330 (FIG. 3). The modeling component 330 can determine a solution to the model inversion problem using one or many of the generated time series of imaging data as observations in a parameter estimation technique. That is, the extractor component 320 can generate estimates of parameters defining the physical model. The extractor component 320 can apply various parameter estimation techniques. Those techniques can include, for example, regression, maximum likelihood estimation, Monte Carlo simulations, or similar. As is shown in Eq. (1), the physical model can include an advection-diffusion model. Accordingly, the modeling component 330 can generate an estimate of <A>, <D>, and <S>. In some configurations, <A>, <D>, and <S> can be determined for a single time-resolved fluorescence profile—e.g., the extractor component 320 can determine a solution to the model inversion problem for each trace in panel 410 in FIG. 4. In addition, or some embodiments, the feature vector 134 can include parameters defining respective features that can be generated directly or indirectly from time-series data.

In some embodiments, rather than relying on an average over spatial coordinates, the modeling component 330 can determine a spatially-resolved (or spatially-distributed) solution to the model inversion problem by using I{(t; x, y)}. In those embodiments, the modeling component 330 can generate estimates of A(x, y), D(x, y), S(x, y), resulting in a feature vector 134 that is spatially-resolved. As an illustration, FIG. 5 presents examples of spatially-resolved parameters S(x, y) A(x, y), D(x, y) of a physical model that can determine time-resolved fluorescence of a dye substance transported through the organ 102, in accordance with one or more embodiments described herein. In addition, or in other embodiments, the feature vector 134 can include parameters defining respective features that can be generated directly or indirectly from time-series data.

In some embodiments, the feature vector 134 also can include user-profile data indicative of various characteristics of a subject having the organ 102 and associated organ tissue. As an example, the user-profile data can include records indicative of a medical history of the subject. The records can indicate, for example, age of the subject, presence or absence of pre-existing conditions, or similar. In those embodiments, the ingestion component 310 (FIG. 3) can obtain the user-profile data from one or more memory devices 150 (referred to as subject data repository 150).

Back to referring to FIG. 1, the candidate identification system 120 also can include a classification component 140 that can generate a classification attribute for the section 104 of organ tissue by applying a classification model 144 to the feature vector 134. As an illustration, the classification model 144 can include one of a random forest model or a convolutional neural network (CNN) model. The classification attribute can designate the section 104 of organ tissue as one of biopsy-candidate or non-biopsy-candidate. The classification attribute can be embodied in, or can include, a label. In this disclosure, the term "label" refers to an indicator of information, such as a textual indicator, a graphical indicator, an aural indicator, or an indicator that combines at least two of the preceding indicators. For purposes of illustration, the label can contain a string of characters that convey that the section 104 of organ tissue is either a biopsy-candidate or a non-biopsy-candidate. Indeed, in one example, the label can be one of "Biopsy-Candidate" or "Non-Biopsy-Candidate." In other examples, the label can include one or a combination of another type of textual element, a graphical element, or an aural element conveying that the section 104 of organ tissue is one of a biopsy-candidate or a non-biopsy-candidate.

In addition, or in some embodiments, the classification component 140 can generate a confidence score for a label that has been generated. The confidence score can be generated concurrently with the generation of the label, in response to the application of the classification model 144 to the feature vector 134. The confidence score can be a real number in the interval [0.1] and represents a probability of the label being accurate.

In some cases, the section 104 of organ tissue can be probed multiple times. In those situations, the feature composition component 130 can receive additional video data 114 representing a second sequence of frames 116. The feature composition component 130 can then generate another feature vector 134 using the second sequence of frames 116. As is discussed above, the second feature 134 can correspond to the entire section 104 or can be a spatially-resolved feature vector 134. Regardless of its type, the second feature vector 134 that can be generated includes second parameters defining the physical model that describes the on-tissue dye dynamics. See Eq. (1) above. The classification component 140 can then update a previous classification attribute by applying the classification model 144 to the second feature vector 134.

The updated classification attribute can be an updated label, e.g., "Biopsy Candidate" or Non-Biopsy-Candidate." In some embodiments, the classification component 140 can generate a second confidence score for the updated label. The second confidence score represents a probability of the updated label being accurate.

In some embodiments, the candidate identification system 120 can supply classification attributes that have been generated. To that end, in some cases, the candidate identification system 120 can determine if a criterion for reporting the classification attribute is satisfied. The criterion can dictate, for example, that reporting occurs when a confidence score generated for a label generated by the classification component 140 exceeds a threshold value (e.g., a real number in the interval [0,1]). The threshold value can be retained in reporting parameter(s) 368 retained in the memory 360 (FIG. 3).

In response to such a criterion being satisfied, in one of those embodiments, the candidate identification system 120 can supply a classification attribute and/or a second classification attribute by sending each one of those attributes to a device remotely located relative to the candidate identification system 120. In some cases, the classification attributes can be sent in essentially real-time, as they become available. In addition, or in another one of those embodiments, the candidate identification system 120 can supply the classification attribute or the second classification attribute by retaining one or both of those attributes in data storage 160 functionally coupled to the candidate identification system 120, and configuring an interface (e.g., an application programming interface (API); not depicted in FIG. 1) to permit access to the retained classification attribute(s). Further, or in yet another one of those embodiments, the candidate identification system 120 can supply the classification attribute by causing a display device to present a visual element indicative of the classification attribute. In one example, the display device can be integrated into the medical imaging equipment 110, and can present the visual element in proximity to another visual element depicting the section 104 or a ROI therein. As is illustrated in FIG. 3, the candidate identification system 120 can include a report component 340 that can supply the classification attributes in accordance with aspects described herein.

The candidate identification system 120 (via the report component 340 (FIG. 3), for example) can supply other types of information. For instance, the candidate identification system 120 can send data defining a boundary demarcating either the section 104 or a ROI therein that has been identified as a biopsy candidate. Such a boundary can demarcate a polygonal area (either regular or irregular) or another area having a periphery of a defined shape, with or without vertices.

Figure 6:
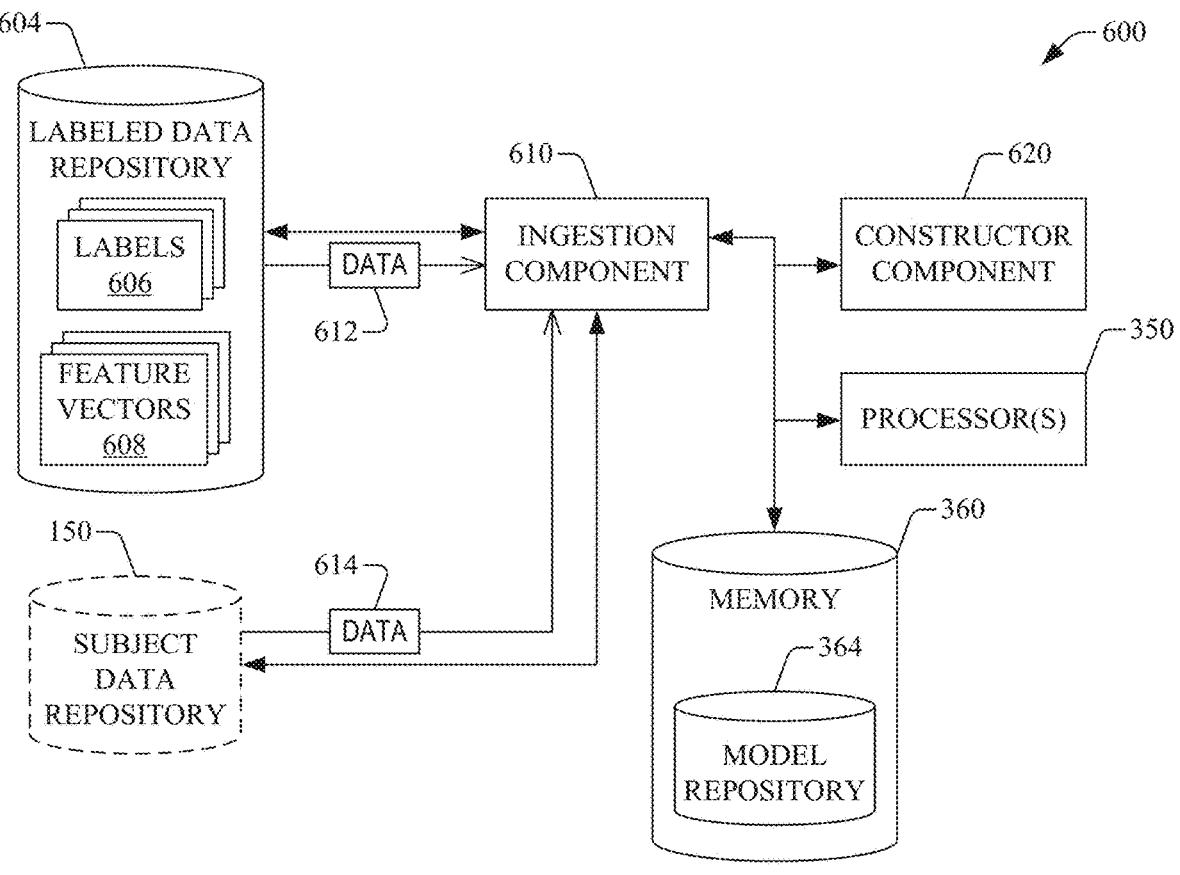
FIG. 6 is a block diagram of a non-limiting example of a system for generation of a classification model to classify a section of organ tissue as either a candidate or a non-candidate for pathology tests, in accordance with one or more embodiments described herein.

FIG. 6 is a block diagram of a non-limiting example of a system 600 for generating a classification model to classify a section of organ tissue as either a candidate or a non-candidate for pathology tests, in accordance with one or more embodiments described herein. As mentioned, the classification model can include one of a random forest model or a CNN model. The system 600 can include an ingestion component 610 that can obtain different types of training data. Because the classification model can be generated to implement a classification task, the ingestion component 610 can obtain different types of labeled data 612 from one or more memory devices 604 (referred to as labeled data repository 604). The labeled data 612 can include a subset of multiple labels 606 retained in the labeled data repository 604. In some embodiments, a label of the multiple labels can include one or a combination of a textual element, a graphical element, or an aural element.

In some embodiments, each label in the subset of multiple labels 606 designates a group of multispectral images of a section of organ tissue. Each label (or, in some embodiments, a group of labels) of the subset of multiple labels 606 can represent one of a biopsy-candidate category or a non-biopsy-candidate category. The labeled data 612 also can include a subset of multiple feature vectors 608 retained in the labeled data repository 604. In some embodiments, each feature vector in the subset of multiple feature vectors 608 corresponds to a single label in the subset of multiple labels 606. A first feature vector of the subset of multiple feature vectors 608 can include parameters defining a physical model representing an on-tissue dye dynamics that determines a time series of imaging data representing a group of multispectral images. In some embodiments, the physical model can include a perfusion model defined, at least partially, by an advection-diffusion equation in two-dimensional space. In addition, or in other embodiments, the physical model also can include a photon diffusion equation describing photon fluence rate distribution across the section 104 or a ROI In some embodiments, the physical model also can include a photon diffusion equation describing photon fluence rate distribution across the section 104 or a ROI contained in the section 104.

Accordingly, by obtaining the subset of multiple feature vectors 608, the ingestion component 610 can receive a first parameter defining an advection vector-field coefficient, a second parameter defining an isotropic diffusion coefficient, and a third parameter defining an intensity of a source of the advection-diffusion equation. The first, second, and third parameters can define the advection-diffusion equation (Eq. (1)) representing the physical model.

The system 600 can include a constructor component 620 that can operate on the data 612 obtained by the ingestion component 610. By operating on the data 612, the constructor component 620 can train the classification model using the subset of the multiple feature vectors 608 and the subset of the multiple labels 606. The classification model can be trained to classify a particular group of multispectral images of the section of organ tissue as pertaining to one of the biopsy-candidate category or the non-biopsy-candidate category. To train the classification model, the constructor component 620 can determine, using the data 612, a solution to an optimization problem with respect to a prediction error function, e.g., a function that yields a value based on an evaluation of differences between known labels for respective feature vectors and predicted labels for the respective feature vectors, the predicted labels being predicted by the classification model. The solution results in model parameters that minimize the prediction error function. The model parameters define a trained classification model. The constructor component 620 can retain the trained classification model in the model repository 364.

In some embodiments, the system 600 also can train the classification model using additional types of data. In at least one of those embodiments, the ingestion component 610 can obtain user-profile data 614 from the subject data repository 150. The user-profile data 614 can include first data indicative of a medical history of a subject corresponding to organ tissue. The constructor component 620 can then train a second classification model using the data 612 and the user-profile data 614. The second classification model also can be trained to classify a particular group of multispectral images of a section of organ tissue as pertaining to one of the biopsy-candidate category or the non-biopsy-candidate category. To train the second classification model, the constructor component 620 can determine, using the data 612 and the user-profile data 614, a solution to an optimization problem with respect to a prediction error function. The solution results in second model parameters that minimize the prediction error function. The second model parameters define a trained second classification model. The constructor component 620 can retain the trained second classification model in the model repository 364.

Figure 7:
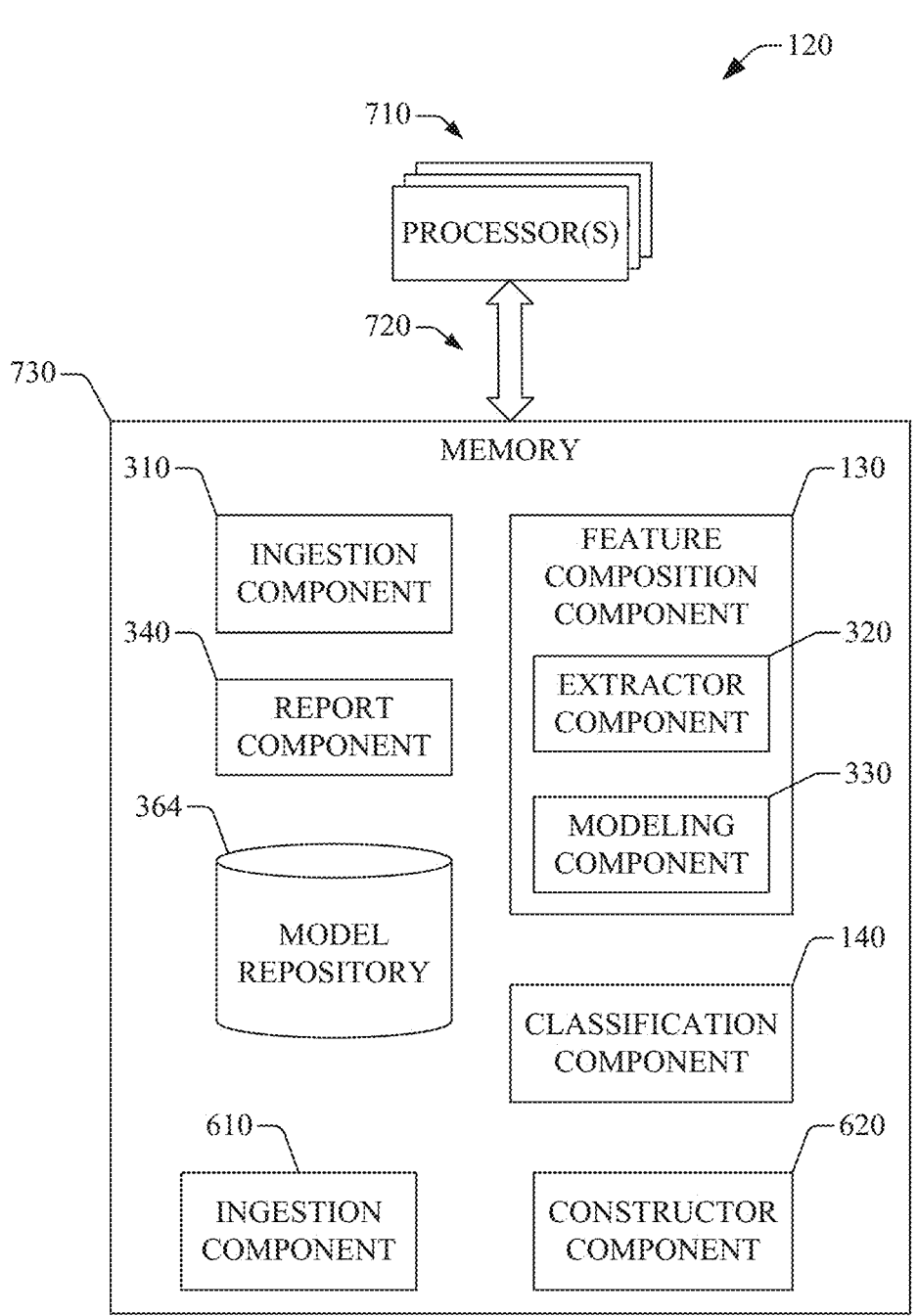
FIG. 7 is a block diagram of a non-limiting example of another system for identification of a section of organ tissue as either a candidate or a non-candidate for pathology tests, in accordance with one or more embodiments described herein.

FIG. 7 presents a block diagram of a non-limiting example of the candidate identification system 120 in accordance with one or more embodiments described herein. As is illustrated in FIG. 7, the candidate identification system 120 can include one or many processors 710 and one or many memory devices 730 (referred to as memory 730). In some embodiments, the processor(s) 710 can be arranged in a single computing apparatus (a blade server device or another type of server device, for example). In other embodiments, the processor(s) 710 can be distributed across two or more computing apparatuses (e.g., multiple blade server devices or other types of server devices).

The one or many processors 710 can be operatively coupled to the memory 730 by means of one or many communication interfaces 720, for example. The communication interface(s) 720 can be suitable for the particular arrangement (localized or distributed) of the processor(s) 710. In some embodiments, the communication interface(s) 720 can include one or many bus architectures, such an Ethernet-based industrial bus, a controller area network (CAN) bus, a Modbus, other types of fieldbus architectures, or the like. In addition, or in other embodiments, the communication interface(s) can include a wireless network and/or a wireline network having respective footprints.

As is illustrated in FIG. 7, the memory 730 can retain or otherwise store therein machine-accessible components (e.g., computer-readable and/or computer-executable components) in accordance with this disclosure. As such, in some embodiments, machine-accessible instructions (e.g., computer-readable and/or computer-executable instructions) embody or otherwise constitute each one of the machine-accessible components within the memory 730. The machine-accessible instructions are encoded in the memory 730 and can be arranged to form each one of the machine-accessible components. The machine-accessible instructions can be built (e.g., linked and compiled) and retained in computer-executable form in the memory 730 (as is shown in FIG. 7) or in one or many other machine-accessible non-transitory storage media. Specifically, as is shown in FIG. 7, in some embodiments, the machine-accessible components include the ingestion component 310, the feature composition component 130, including the extractor component 320 and the modeling component 330, the classification component 140, the report component 340, the ingestion component 610, and the constructor component 620. As is also shown in FIG. 7, the memory 730 also can include the model repository 364 and at least some of the data retained therein.

The machine-accessible components, individually or in a particular combination, can be accessed and executed by at least one of the processor(s) 710. In response to execution, each one of the machine-accessible components can provide the functionality described herein. Accordingly, execution of the computer-accessible components retained in the memory 730 can cause the candidate identification system 120 to operate in accordance with aspects described herein. More concretely, at least one of the processor(s) 710 can execute the machine-accessible components to cause the candidate identification system 120 to permit the identification of a section of organ tissue as either a candidate or a non-candidate for pathology tests, in accordance with aspects of this disclosure.

Although not illustrated in FIG. 7, the candidate identification system 120 also can include other types of computing resources that can permit or otherwise facilitate the execution of the machine-accessible components retained in the memory 730. Those computing resources can include, for example, central processing units (CPUs), graphics processing units (GPUs), tensor processing units (TPUs), memory, disk space, incoming bandwidth, and/or outgoing bandwidth, interface(s) (such as I/O interfaces); controller devices(s); power supplies; and the like. For instance, the memory 730 also can include programming interface(s) (such as APIs); an operating system; software for configuration and or control of a virtualized environment; firmware; and the like.

Figure 8:
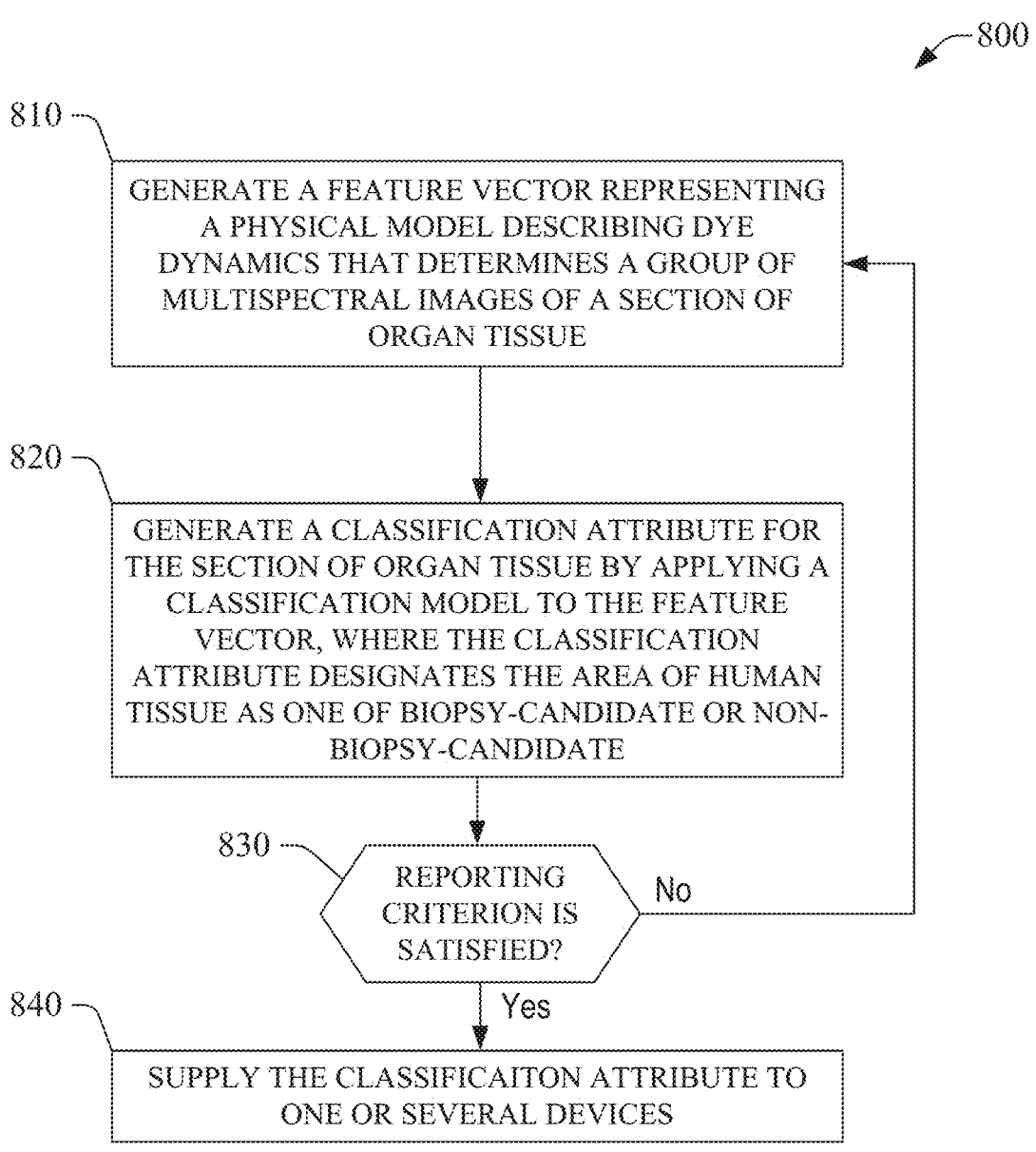
FIG. 8 is a flowchart of a non-limiting example of a computer-implemented method for identifying a section of organ tissue as either a candidate on a non-candidate for pathology tests, in accordance with one or more embodiments described herein.

FIG. 8 is a flowchart of a non-limiting example of a computer-implemented method for identifying a section of organ tissue as either a candidate on a non-candidate for pathology tests, in accordance with one or more embodiments described herein. A computing system can implement, at least partially, the computer-implemented method 800. Implementing the computer-implemented method 800 can include compiling or executing, or both, one or several of the blocks included in the method 800, for example. The computing system can include and/or can be operatively coupled to one or many processors, one or more memory devices, other types of computing resources (such as communication interface(s)), a combination thereof, or similar. In some embodiments, the computing system can be embodied in, or can constitute, the candidate identification system 120 in accordance with the various embodiments disclosed herein.

At block 810, the computing system can generate (via the feature composition component 130 (FIG. 1), for example) a feature vector representing a physical model describing dye dynamics that determines a group of multispectral images of a section of organ tissue. The feature vector can include parameters defining the physical model. The feature vector can be generated via the feature composition component 130, in some cases. In one example, the computing system can execute the feature composition component 130 to generate the feature vector.

To generate the feature vector, the computing system can generate a time series of imaging data using the group of multispectral images of the section of organ tissue. As is described herein, the imaging data can be determined from the group of multispectral images. Thus, the dye dynamics determines the time series of imaging data. The time series of imaging data can include, in some embodiments, spatially-resolved time series of fluorescence intensities over a grid of points in a two-dimensional region relative to a coordinate system at the section of organ tissue (e.g., section 104 (FIG. 1) or an ROI therein). The computing system can generate the time series via the extractor component 320 (FIG. 3), in some cases. Further, also to generate the feature vector, the computing system can generate (via the modeling component 330, for example) estimates of parameters defining the physical model. For instance, as is described herein, the physical model can include an advection-diffusion model, and the computing system can generate an estimate of a source distribution for the physical model in the two-dimensional region. See Eq. (1) above, for example.

At block 820, the computing system can generate (via the classification component 140 (FIG. 1), for example) a classification attribute for the section of organ tissue by applying a classification model to the feature vector. The classification attribute can designate the section of organ tissue as one of biopsy-candidate or non-biopsy-candidate. The classification attribute can be generated via the classification component 140, in some cases. In one example, the computing system can execute the classification component 140 to generate the classification attribute. As mentioned, the classification attribute can be embodied in, or can include, a label. In one example, the label can be either "Biopsy-Candidate" or "Non-Biopsy-Candidate." Although not illustrated in FIG. 8, in some embodiments, the example computer-implemented method 800 can include generating a confidence score for the label. The confidence score represents a probability of the label being accurate.

At block 830, the computing system can determine (via the report component 340 (FIG. 3), for example) if a criterion for reporting the classification attribute is satisfied. In some cases, the criterion can dictate that reporting occurs when a confidence score generated for a label exceeds a threshold value (e.g., a real number in the interval [0,1]). As mentioned, the threshold value can be retained in reporting parameter(s) 368 retained in the memory 360. In response to a negative determination, the flow of the example computer-implemented method 800 can return to block 810.

In response to the criterion being satisfied, the flow of the example computer-implemented method 800 can continue to block 840, at which block, the computing system can supply (via the report component 340 (FIG. 3), for example) the classification attribute. In one embodiment, supplying the classification attribute and/or the second classification attribute can include sending the classification attribute, as it becomes available. to a device remotely located relative to the computing system. In addition, or in another embodiment, supplying the classification attribute can include retaining the classification attribute in data storage (e.g., memory 360) and configuring an interface (e.g., an application programming interface (API)) to permit access to the retained classification attribute. Further, or in yet other embodiments, supplying the classification attribute can include causing a display device to present a visual element indicative of the classification attribute. In one example, the display device can be integrated into the medical imaging equipment 110 and can present the visual element in proximity to another visual element depicting the section of organ tissue.

In some situations, as mentioned, the section of organ tissue (e.g., section 104 (FIG. 1) or an ROI therein) can be probed multiple times. In those situations, the example computer-implemented method 800 can be reiterated in order to update the classification attribute. Thus, the computing system can generate (via the feature composition component 130, for example) a second feature vector including second parameters defining the physical model that determines a second time series of imaging data representing a second group of multispectral images of the section of organ tissue. The computing system can then update (via the classification component 140, for example) the classification attribute by applying the classification model to the second feature vector.

FIG. 9 is a flowchart of a non-limiting example of a computer-implemented method 900 for generating a classification model for classification of a section of organ tissue as either a candidate on a non-candidate for a pathology test, in accordance with one or more embodiments described herein. A computing system can implement, at least partially, the computer-implemented method 900. Implementing the computer-implemented method 900 can include compiling or executing, or both, one or several of the blocks included in the computer-implemented method 900, for example. The computing system that can implement the example computer-implemented method 800 also can implement the example computer-implemented method 900. The computing system can include and/or can be operatively coupled to one or many processors, one or more memory devices, other types of computing resources (such as communication interface(s)), a combination thereof, or similar. In some embodiments, the computing system can be embodied in, or can constitute, the candidate identification system 120 in accordance with the various embodiments disclosed herein.

At block 910, the computing system can receive (via the ingestion component 610 (FIG. 6), for example) multiple labels designating respective groups of multispectral images of a section of organ tissue. Each label of the multiple labels can represent one of a biopsy-candidate category or a non-biopsy-candidate category. Each label corresponds to the section of organ tissue probed to generate a group of the groups of multispectral images.

At block 920, the computing system can receive (also via the ingestion component 610 (FIG. 6), in some cases) multiple feature vectors. As mentioned, a first feature vector of the multiple feature vectors can include parameters defining a physical model representing an on-tissue dye dynamics that can determine a time series of imaging data representing a first group of the groups of multispectral images. In some embodiments, the physical model can include a perfusion model defined, at least partially, by an advection-diffusion equation in two-dimensional space. See Eq. (1), for example. In addition, or in other embodiments, the physical model also can include a photon diffusion equation describing photon fluence rate distribution across the section of organ tissue. Accordingly, receiving the multiple feature vectors can include receiving a first parameter defining an advection vector-field coefficient, a second parameter defining an isotropic diffusion coefficient, and a third parameter defining an intensity of a source of the advection-diffusion equation. In addition, or in some embodiments, receiving the multiple feature vectors can include receiving parameters defining respective features that can be generated directly or indirectly from the time-series data.

At block 930, the computing system can train (via the constructor component 620 (FIG. 6), for example) a classification model using the multiple feature vectors and the multiple labels. The classification model can be trained to classify a particular group of the groups of multispectral images as pertaining to one of the biopsy-candidate category or the non-biopsy-candidate category.

The computing system also can train the classification model using additional types of data. In some embodiments, the computing system can receive (via the ingestion component 610 (FIG. 6) for example) user-profile data including records indicative of a medical history of a subject corresponding to the organ tissue. The computing system can then train (via the constructor component 610 (FIG. 6), for example) a second classification model using the multiple feature vectors, the user-profile data, and the multiple labels. The second classification model is trained to classify a particular group of the groups of multispectral images as pertaining to one of the biopsy-candidate category or the non-biopsy-candidate category.

Figure 10:
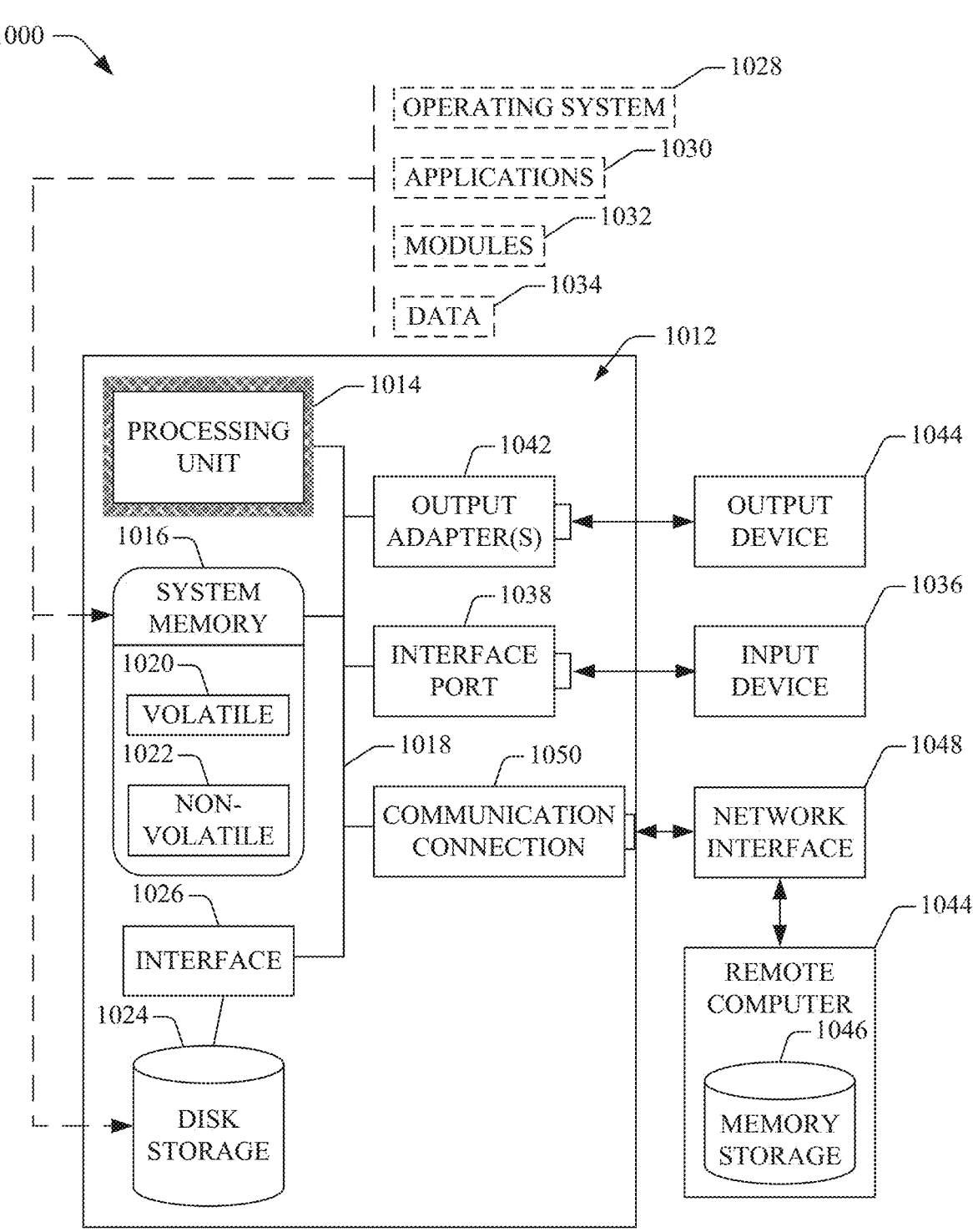
FIG. 10 is a block diagram of a non-limiting example of an operating environment in which one or more embodiments described herein can be implemented.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program prod-ucts according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Figure 11:
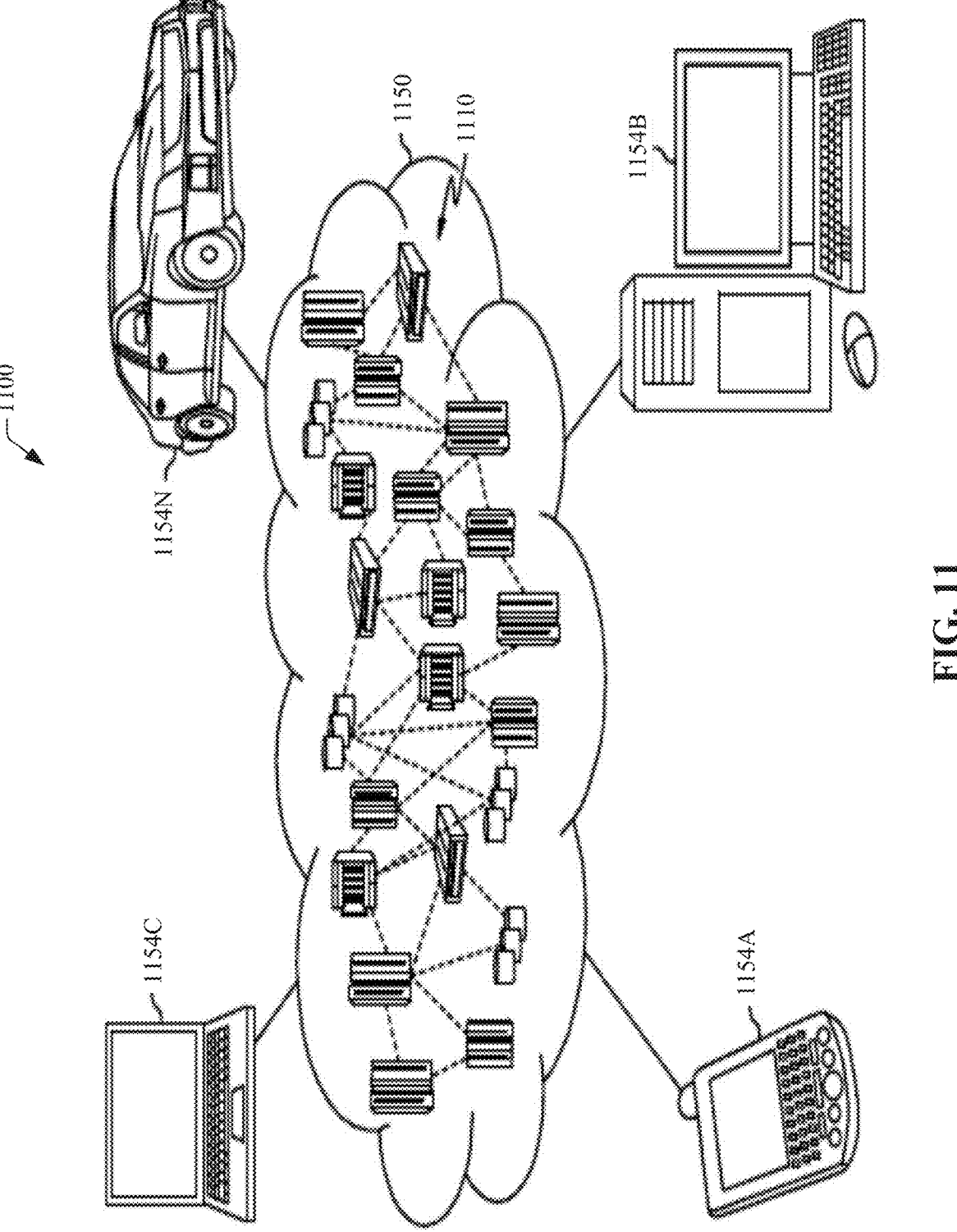
FIG. 11 is a block diagram of a non-limiting example of a cloud computing environment in accordance with one or more embodiments described herein.

In some embodiments, the various embodiments of candidate identification system 120 described herein can be associated with a cloud computing environment. For example, candidate identification system 120 can be associated with cloud computing environment 1150 as is illustrated in FIG. 11 and/or one or more functional abstraction layers described herein with reference to FIG. 12 (e.g., hardware and software layer 1260, virtualization layer 1270, management layer 1280, and/or workloads layer 1290).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 11 an illustrative cloud computing environment 1150 is depicted. As shown, cloud computing environment 1150 includes one or more cloud computing nodes 1110 with which local computing devices used by cloud consumers, such as, for example, personal digital assistant (PDA) or cellular telephone 1154A, desktop computer 1154B, laptop computer 1154C, and/or automobile computer system 1154N may communicate. Although not illustrated in FIG. 11, cloud computing nodes 1110 can further comprise a quantum platform (e.g., quantum computer, quantum hardware, quantum software, and/or another quantum platform) with which local computing devices used by cloud consumers can communicate. Nodes 1110 may communicate with one another. They may be grouped (not shown) physically or virtually, in one or more networks, such as Private, Community, Public, or Hybrid clouds as described hereinabove, or a combination thereof. This allows cloud computing environment 1150 to offer infrastructure, platforms and/or software as services for which a cloud consumer does not need to maintain resources on a local computing device. It is understood that the types of computing devices 1154A-N shown in FIG. 11 are intended to be illustrative only and that computing nodes 1110 and cloud computing environment 1150 can communicate with any type of computerized device over any type of network and/or network addressable connection (e.g., using a web browser).

Figure 12:
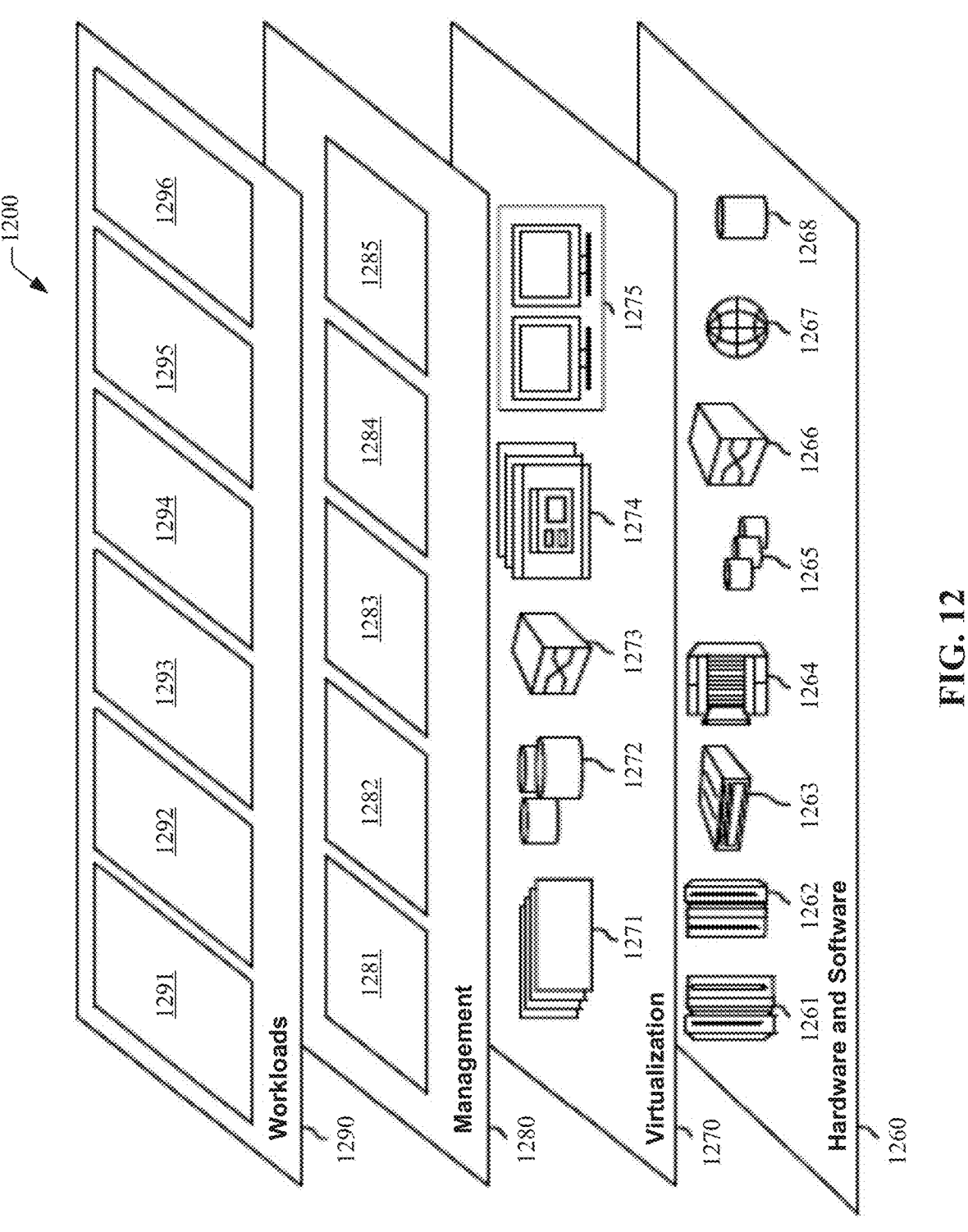
FIG. 12 is a block diagram of a non-limiting example of abstraction model layers in accordance with one or more embodiments described herein.

Referring now to FIG. 12, a set of functional abstraction layers provided by cloud computing environment 1150 (FIG. 11) is shown. It should be understood in advance that the components, layers, and functions shown in FIG. 12 are intended to be illustrative only and embodiments of the invention are not limited thereto. As depicted, the following layers and corresponding functions are provided:

Hardware and software layer 1260 include hardware and software components. Examples of hardware components include: mainframes 1261; RISC (Reduced Instruction Set Computer) architecture based servers 1262; servers 1263; blade servers 1264; storage devices 1265; and networks and networking components 1266. In some embodiments, software components include network application server software 1267, database software 1268, quantum platform routing software (not illustrated in FIG. 12), and/or quantum software (not illustrated in FIG. 12).

Virtualization layer 1270 provides an abstraction layer from which the following examples of virtual entities may be provided: virtual servers 1271; virtual storage 1272; virtual networks 1273, including virtual private networks; virtual applications and operating systems 1274; and virtual clients 1275.

In one example, management layer 1280 may provide the functions described below. Resource provisioning 1281 provides dynamic procurement of computing resources and other resources that are utilized to perform tasks within the cloud computing environment. Metering and pricing 1282 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1283 provides access to the cloud computing environment for consumers and system administrators. Service level management 1284 provides cloud computing resource allocation and management such that required service levels are met. Service Level Agreement (SLA) planning and fulfillment 1285 provide pre-arrangement for, and procurement of, cloud computing resources for which a future requirement is anticipated in accordance with an SLA.

Workloads layer 1290 provides examples of functionality for which the cloud computing environment may be utilized. Non-limiting examples of workloads and functions which may be provided from this layer include: mapping and navigation 1291; software development and lifecycle management 1292; virtual classroom education delivery 1293; data analytics processing 1294; transaction processing 1295; and vulnerability risk assessment software 1296.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units.

In this disclosure, terms such as "store," "storage," "data store," data storage," "database," "repository," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a processor that executes computer-executable components stored in memory, the computer-executable component comprising:
medical imaging equipment that generates a group of multispectral images of a section of bodily tissue by emitting excitation light onto the bodily tissue and collecting emitted light from a dye substance transported through the bodily tissue;
a feature composition component that generates a feature vector representing a physical model describing on-tissue dye dynamics based on the multispectral images, wherein the feature composition component:
extracts a spatially-resolved time series of intensities of the emitted light over a grid of points in a two-dimensional region corresponding to the section of bodily tissue; and comprises estimates of parameters of an advection-diffusion equation describing the on-tissue dye dynamics, the parameters including an advection coefficient, an isotropic diffusion coefficient, and a source distribution, the estimates being obtained by inverting the advection-diffusion equation based on the spatially-resolved time series; and
a classification component that generates a classification attribute for the section of bodily tissue by applying a classification model to the feature vector, wherein the classification attribute designates the section of bodily tissue as one of biopsy-candidate or non-biopsy-candidate for pathology testing.

2. The system of claim 1, wherein the feature composition component generates a second feature vector including second parameters defining the physical model representing the on-tissue dye dynamics that determines a second time series of imaging data representing a second group of multispectral images of the section of bodily tissue; and
the classification component updates the classification attribute by applying the classification model to the second feature vector.

3. The system of claim 1, wherein the classification attribute comprises a label, and wherein the classification component further generates a confidence score for the label, wherein the confidence score represents a probability of the label being accurate.

4. The system of claim 1, further comprising a report component that:
determines, using the confidence score, that a reporting criterion is satisfied; and
causes a display device to present the classification attribute.

5. The system of claim 1, further comprising an extractor component that generates the time series of imaging data using the group of multispectral images of the section of bodily tissue, the time series of imaging data including spatially-resolved time series of fluorescence intensities in a grid of points in a two-dimensional region relative to a coordinate system at the section of bodily tissue.

6. The system of claim 5, wherein the extractor component selects a spatial resolution and determines brightness intensities for respective points in a two-dimensional grid of points within a multispectral image of the section of bodily tissue at a defined time, the two-dimensional grid of points having a pitch defined by the spatial resolution, and wherein determining the brightness intensities comprises averaging observed brightness values within the two-dimensional grid of points in an multispectral image of the section of bodily tissue at a defined time.

7. The system of claim 5, further comprising a modeling component that generates estimates of a source distribution in the two-dimensional region of the physical model, the source distribution determining, at least partially, the spatially-resolved time series of fluorescence intensities.

8. A computer-implemented method, comprising:
generating, by a computer system operatively coupled to a processor, a group of multispectral images of a section of bodily tissue by emitting excitation light onto the bodily tissue and collecting emitted light from a dye substance transported through the bodily tissue;
generating, by the computing system, a feature vector representing a physical model describing on-tissue dye dynamics based on the multispectral images, the generating comprising:

extracting a spatially-resolved time series of intensities of the emitted light over a grid of points in a two-dimensional region corresponding to the section of bodily tissue; and estimating parameters of an advection-diffusion equation describing the on-tissue dye dynamics, the parameters including an advection coefficient, an isotropic diffusion coefficient, and a source distribution, the estimating comprising inverting the advection-diffusion equation based on the spatially-resolved time series to obtain the feature vector; and generating, by the computing system, a classification attribute for the section of bodily tissue by applying a classification model to the feature vector, wherein the classification attribute designates the section of bodily tissue as one of biopsy-candidate or non-biopsy-candidate for pathology testing.

9. The computer-implemented method of claim 8, further comprising:

generating, by the computing system, a second feature vector representing the on-tissue dye dynamics that determines a second group of multispectral images of the section of bodily tissue; and updating, by the computing system, the classification attribute by applying the classification model to the second feature vector.

10. The computer-implemented method of claim 8, wherein the classification attribute comprises a label, the method further comprising generating a confidence score for the label, wherein the confidence score represents a probability of the label being accurate.

11. The computer-implemented method of claim 8, wherein the generating comprises generating a time series of imaging data using the group of multispectral images of the section of bodily tissue, the time series of imaging data including spatially-resolved time series of fluorescence intensities over a grid of points in a two-dimensional region relative to a coordinate system fixed to the section of bodily tissue.

12. The computer-implemented method of claim 11, wherein generating the time series comprises:

selecting a spatial resolution; and determining brightness intensities for respective points in a two-dimensional grid of points within a multispectral image of the section of bodily tissue at a defined time, the two-dimensional grid of points having a pitch defined by the spatial resolution, wherein determining the brightness intensities comprises averaging observed brightness values within the two-dimensional grid of points.

13. The computer-implemented method of claim 11, further comprising generating estimates of a source distribution in the two-dimensional region of the physical model, the source distribution determining, at least partially, the spatially-resolved time series of fluorescence intensities.

14. A system, comprising:

a processor that executes computer-executable components stored in memory, the computer-executable component comprising:

medical imaging equipment that generates a first group of groups of multispectral images of a section of bodily tissue by emitting excitation light onto the bodily tissue and collecting emitted light from a dye substance transported through the bodily tissue;

an ingestion component that receives multiple feature vectors representing respective physical models describing on-tissue dye dynamics, wherein a first feature vector of the multiple feature vectors corresponds to a first group of multispectral images and is generated by:

extracting a spatially-resolved time series of intensities of the emitted light over a grid of points in a two-dimensional region corresponding to the section of bodily tissue; and estimating parameters of an advection-diffusion equation describing the on-tissue dye dynamics, the parameters including an advection coefficient, an isotropic diffusion coefficient, and a source distribution, the estimating comprising inverting the advection-diffusion equation based on the spatially-resolved time series to obtain the first feature vector, wherein each feature vector of the multiple feature vectors is obtained by performing the extracting and estimating operations on a respective group of the groups of multispectral images; and a constructor component that trains, using the multiple feature vectors, a classification model to classify a particular group of the groups of multispectral images as pertaining to one of a biopsy-candidate category or a non-biopsy-candidate category.

15. The system of claim 14, wherein the ingestion component receives user profile data indicative of a medical history of a subject corresponding to the section of bodily tissue; and wherein the constructor component trains, using the multiple feature vectors and the user profile data, a second classification model to classify the particular group as pertaining to one of the biopsy-candidate category or the non-biopsy-candidate category.

16. The system of claim 14, wherein the physical model is defined, at least partially, by an advection-diffusion equation in two-dimensional space, and wherein the receiving the multiple feature vectors comprises receiving a first parameter defining an advection vector-field coefficient, a second parameter defining an isotropic diffusion coefficient, and a third parameter defining a source of the advection-diffusion equation.

17. A computer-implemented method, comprising:

receiving, by a computing system operatively coupled to a processor, multiple feature vectors representing respective physical models describing on-tissue dye dynamics, wherein a first feature vector of the multiple feature vectors corresponds to a first group of groups of multispectral images of a section of bodily tissue generated by emitting excitation light onto the bodily tissue and collecting emitted light from a dye substance transported through the bodily tissue, and wherein generating the first feature vector comprises:

extracting a spatially-resolved time series of intensities of the emitted light over a grid of points in a two-dimensional region corresponding to the section of bodily tissue; and estimating parameters of an advection-diffusion equation describing the on-tissue dye dynamics, the parameters including an advection coefficient, an isotropic diffusion coefficient, and a source distribution, the estimating comprising inverting the advection-diffusion equation based on the spatially-resolved time series to obtain the first feature vector, and wherein each feature vector of the multiple feature vectors is obtained by performing the extracting and estimating operations on a respective group of the groups of multispectral images; and training, by the computing system and using the multiple feature vectors, a classification model to classify a particular group of multispectral images as pertaining to one of a biopsy-candidate category or a non-biopsy-candidate category.

18. The computer-implemented method of claim 17, further comprising:

receiving, by the computing system, user profile data indicative of a medical history of a subject corresponding to the section of bodily tissue;

training, by the computing system, using the multiple feature vectors and the user profile data, a second classification model to classify the particular group as pertaining to one of the biopsy-candidate category or the non-biopsy-candidate category.

19. The computer-implemented method of claim 17, wherein the physical model is defined, at least partially, by an advection-diffusion equation in two-dimensional space, and wherein the receiving the multiple feature vectors comprises receiving a first parameter defining an advection vector-field coefficient, a second parameter defining an isotropic diffusion coefficient, and a third parameter defining a source of the advection-diffusion equation.

20. A computer program product for identification of a section of a bodily tissue as either a candidate or a non-candidate for a pathology test, the computer program product comprising a computer-readable storage medium having program instructions embodied therewith, the program instructions executable by a processor to cause the processor to:

generate, by the processor, a group of multispectral images of the section of bodily tissue by emitting excitation light onto the bodily tissue and collecting emitted light from a dye substance transported through the bodily tissue;

generate, by the processor, a feature vector representing a physical model describing on-tissue dye dynamics based on the multispectral images, the generating comprising:

extracting a spatially-resolved time series of intensities of the emitted light over a grid of points in a two-dimensional region corresponding to the section of bodily tissue; and estimating parameters of an advection-diffusion equation describing the on-tissue dye dynamics, the parameters including an advection coefficient, an isotropic diffusion coefficient, and a source distribution, the estimating comprising inverting the advection-diffusion equation based on the spatially-resolved time series to obtain the feature vector; and generate, by the processor, a classification attribute for the section of bodily tissue by applying a classification model to the feature vector, wherein the classification attribute designates the section of bodily tissue as one of biopsy-candidate or non-biopsy-candidate.

21. The computer program product of claim 20, wherein the program instructions are further executable by the processor to cause the processor to:

generate, by the processor, a second feature vector representing the physical model describing the dye dynamics that determines a second group of multispectral images of the section of bodily tissue; and update, by the processor, the classification attribute by applying the classification model to the second feature vector.

22. The computer program product of claim 20, wherein the classification attribute comprises a label, and wherein the program instructions are further executable by the processor to cause the processor to generate a confidence score for the label, wherein the confidence score represents a probability of the label being accurate.

23. The computer program product of claim 22, wherein the program instructions are further executable by the processor to cause the processor to:

determine, by the processor, using the confidence score, that a reporting criterion is satisfied; and cause, by the processor, a display device to present the classification attribute.

24. The computer program product of claim 20, wherein the program instructions are further executable by the processor to cause the processor to generate a time series of imaging data using the group of multispectral images of the section of bodily tissue, the time series of imaging data including spatially-resolved time series of fluorescence intensities over a grid of points in a two-dimensional region relative to a coordinate system fixed to the section of bodily tissue.

25. The computer program product of claim 24, wherein the program instructions are further executable by the processor to cause the processor to generate estimates of a source distribution in the two-dimensional region of the physical model, the source distribution determining, at least partially, the spatially-resolved time series of fluorescence intensities.

* * * * *